United States Patent [19]
Shozo et al.

[11] Patent Number: 6,033,087
[45] Date of Patent: Mar. 7, 2000

[54] LED ILLUMINATING DEVICE FOR PROVIDING A UNIFORM LIGHT SPOT

[75] Inventors: Hitora Shozo, Kitakatsuragi-gun; Tokio Kawashima, Yao, both of Japan

[73] Assignee: Patlite Corporation, Osaka, Japan

[21] Appl. No.: 08/997,596

[22] Filed: Dec. 23, 1997

[30] Foreign Application Priority Data

Dec. 26, 1996 [JP] Japan .................................. 8-357600

[51] Int. Cl.⁷ ................................................... F21V 5/02
[52] U.S. Cl. ........................... 362/244; 362/19; 362/33; 362/231; 362/800
[58] Field of Search ........................... 362/19, 33, 231, 362/244, 246, 800

[56] References Cited

U.S. PATENT DOCUMENTS

| | | | |
|---|---|---|---|
| 4,947,291 | 8/1990 | McDermott | 362/231 X |
| 5,039,832 | 8/1991 | Polacek et al. | 362/246 X |
| 5,400,229 | 3/1995 | Lin | 362/800 X |
| 5,580,163 | 12/1996 | Johnson, II | 362/800 X |
| 5,685,637 | 11/1997 | Chapman et al. | 362/244 X |
| 5,690,417 | 11/1997 | Polidor et al. | 362/800 X |

*Primary Examiner*—Laura K. Tso
*Attorney, Agent, or Firm*—Koda & Androlia

[57] ABSTRACT

An illuminating device including a cylindrical main body that is provided with a circularly arranged plurality of LEDs of different colors so as to be used in, for instance, an optical inspection apparatus. The illuminating device further includes a light diffusing element, light-condensing lens and a polarizing element or a prism having polarizing surfaces, which are all installed inside the cylindrical main body. The LED lights are corrected in intensity to be even by the light-diffusing element, pass through the light-condensing lens and further pass through the prism so as to be directed toward a single point and form a superimposed light illuminating an object, thus a CCD camera that is provided in the center of the cylindrical main body can take an image of the object.

10 Claims, 4 Drawing Sheets

LED ILLUMINATING DEVICE FOR PROVIDING A UNIFORM LIGHT SPOT

BACKGROUND OF THE INVENTION

1. Field of the Invention

The present invention relates to an illuminating device that uses LEDs (light emitting diodes) as a light source and more particularly to an LED illuminating device used for, for instance, visual inspection purposes.

2. Prior Art

Illuminating light sources such as fluorescent lamps and halogen light bulbs, etc. have been used in various conventional illuminating devices for the inspection of lead bending, directional discrimination of polarity marks or discrimination of molding defects or cracking in semiconductor manufacturing devices, for dimensional inspection or inspection for scratches in glass and metal product manufacturing lines, etc. Such illuminating devices are also used by being incorporated into an inspection apparatus for inspecting foodstuffs and drug products such as tablets, etc.

However, such light sources generally have problems. They generate a large amount of heat, they have poor resistance to vibration, and they consume a large amount of power. In addition, illuminating devices which use such light sources require the replacement of burned-out lamps, and they are generally large in size. In addition, there is a large variation in the quantity of light caused by voltage fluctuations. Thus, such light sources are not quite adequate in terms of practical utility.

Accordingly, a change from conventional light sources to illuminating devices that use LED light sources has been tentatively explored as a means to solve the problems above.

However, LEDs generally emit only a small quantity of light. It is, therefore, necessary to use means for compensating for this small light quantity. One way is to increase the number of LEDs to be used, and it is also effective to use condensing type LEDs. Various types of lenses have also been employed to condense and diffuse the illuminating light with various types of lenses, thus increasing the apparent size of the light source. These methods are usually used singularly or in combinations.

FIG. 4 illustrates a construction of a conventional illumination device disclosed in Japanese Utility Model Application Laid-Open (Kokai) No. 6-68205.

In this structure, four spot illuminating means 91 are installed on an attachment plate 92 so that these spot illuminating means 91 are inclined toward the center axis, thus producing superimposed LED spotlight 93. In this case, however, correction of the angles of the spot illuminating means 91 is required, and each illuminating means are also large in size.

Currently, monochromatic LEDs of various colors such as red LEDs, yellow LEDs, green LEDs and blue LEDs have been proposed; and such LEDs are used as an illuminating light source for obtaining a specific color light. In the case of these illuminating light sources used for inspections of, for instance, a bend in the leads of a semiconductor device, there is an optimal color of illumination and light quantity depending upon each object to be inspected. In this regard, the problem with the monochromatic LED illuminating devices is that such devices cannot be used as all-purpose light sources for various types of inspections. This is because in cases where visual recognition is accomplished by inspecting digitalized images from, for instance, a CCD camera, it is essential to obtain a high contrast in order to improve the precision of inspection.

Furthermore, in the device shown in FIG. 4, the distribution of the illumination that is projected onto the illuminated surface from the spot illuminating means 91 tends to vary. The reason for this is that the illumination distribution of the LEDs themselves is affected by the internal LED chips and by the shape of the resin molding, etc. that surrounds the LED chips; in addition, if there are differences among respective colors, or even in LEDs of the same type, such differences can cause irregularities in the illumination distribution such as irregularities in the illuminated area and intensity of illumination. Furthermore, there may also be irregularities in the intensity of illumination obtained for reasons related to the structure of the LEDs, e. g., the forming of an image of the internal LED chip on the illuminated surface, etc. For such reasons, even if spotlight are obtained by collecting LED light "as is", there is some unevenness in the illumination distribution of the spotlights depending on the individual LEDs.

Consequently, in the prior art described above, because of irregular illumination in the superimposed LED spotlights 93, and also because of the presence of excess illuminating light in the areas where the spotlights are not superimposed, a high contrast is not obtained, and there is a lack of sharpness in the visual recognition characteristics.

SUMMARY OF THE INVENTION

Accordingly, the object of the present invention is to provide an illuminating device which uses LED light sources with a simple construction that is free of illumination irregularities.

It is another object of the present invention to provide an LED illuminating device which makes it possible to obtain any desired color of illumination so that the illumination device can be used as an all-purpose light source for various types of inspection apparatuses.

The above object is accomplished by a unique structure for an LED illuminating device of the present invention which includes: an LED assembly on which a plurality of LEDs are mounted in a prescribed arrangement; a polarizing optical element which is installed so as to face the plurality of LEDs; and a holding means in which the LED assembly and polarizing optical element are installed; wherein the LED illuminating light beams are superimposed at a prescribed focal distance.

The above-object is accomplished by another unique structure for an LED illuminating device of the present invention which includes: an LED assembly on which a plurality of LEDs are mounted in a prescribed arrangement; a polarizing optical element which is installed so as to face the plurality of LEDs; a condensing optical element provided between the LEDs and the polarizing optical element; and a holding means in which the LED assembly, condensing optical element and polarizing optical element are installed; wherein the LED illuminating light beams are superimposed at a prescribed focal distance.

The above-object is accomplished by still another unique structure for an LED illuminating device of the present invention which includes: an LED assembly on which a plurality of LEDs are mounted in a prescribed arrangement; a polarizing optical element which is installed so as to face the plurality of LEDs; a diffusing optical element, a partially light-blocking element and a condensing optical element which are provided between the LEDs and the polarizing optical element; and a holding means for holding the LED assembly, diffusing optical element, partially light-blocking element, condensing optical element and polarizing optical element; wherein the LED illuminating light beams are superimposed at a prescribed focal distance.

In the above structures of the present invention, the polarizing optical element is a polarizing prism which has a first polarizing surface formed on the light source side and a second polarizing surface formed on the side that faces the surface to be illuminated by the LEDs. In addition, LEDs of different colors are employed in combination, and a control means is further provided so that the quantity of light of the LEDs is controlled on an individual basis or by color groups.

DETAILED DESCRIPTION OF THE INVENTION

Figure 1:
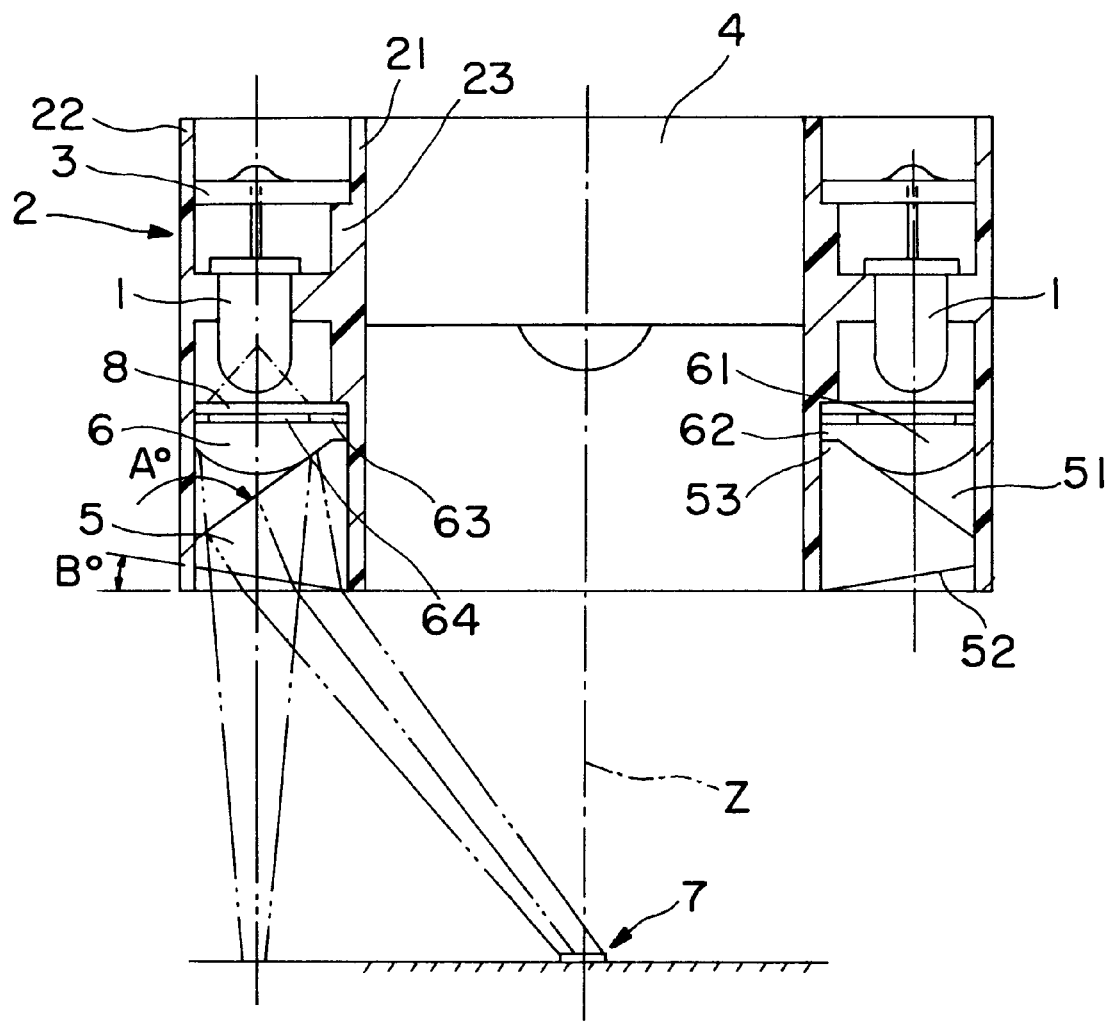
FIG. 1 is a sectional view of the essential parts of an LED illuminating device according to one embodiment of the present invention.

In FIG. 1, the reference numeral 1 indicates LED (light emitting diode) elements which constitute illuminating light sources. Each of these LED elements (eight LEDs in this embodiment) is an LED lamp in which a resin-molded LED is provided with a lead frame leg, and a plurality of these LED lamps are soldered to an LED substrate 3 so as to form an LED assembly, which is incorporated in a feeder circuit.

Figure 2:
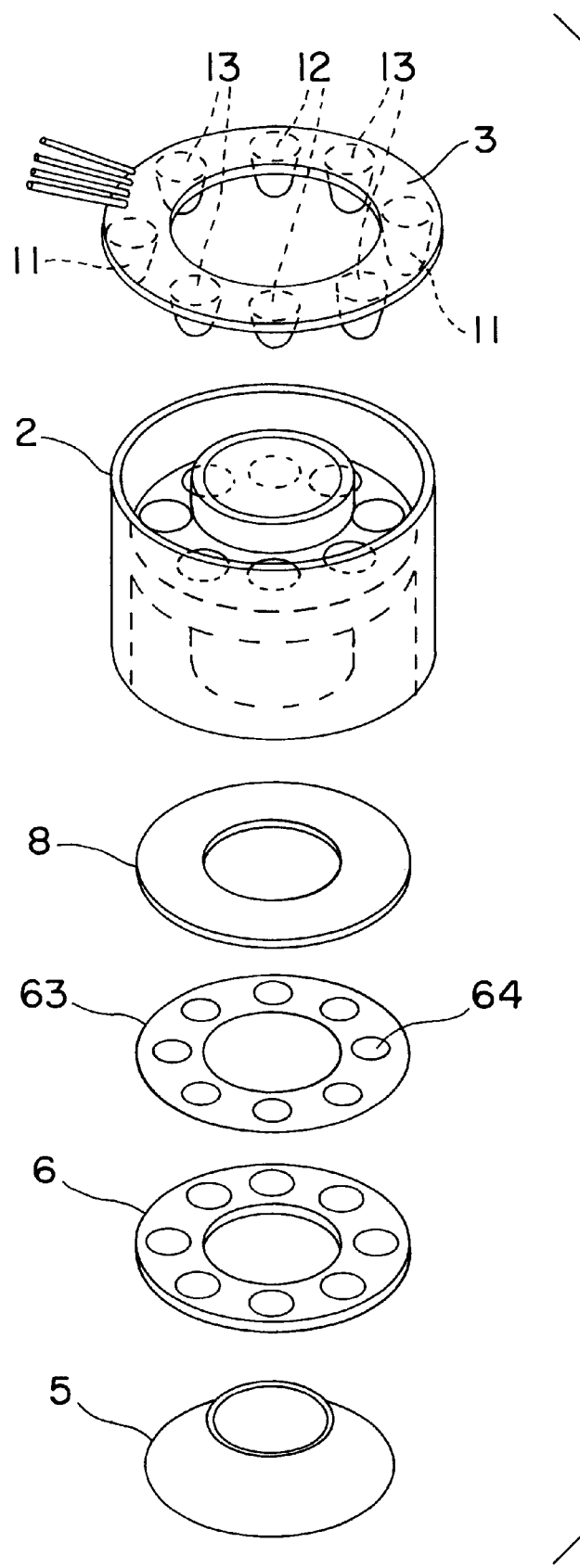
FIG. 2 is an exploded perspective view of the LED illuminating device.

The LED elements 1 are of different colors, i.e., red, blue and green; and they are arranged as shown in FIG. 2. In particular, as seen from FIG. 2, LEDs of respective colors are installed at uniform intervals in a circular arrangement in the following order in a clockwise direction from the upper portion (in FIG. 2) of the LED substrate 3: blue LED 12, green LED 13, red LED 11, green LED 13, blue LED 12, green LED 13, red LED 11, and green LED 13. The reason that the green LEDs 13 are used more than the LEDs of other colors is that the green LEDs have a lower brightness compared to the red and blue LEDs. The respective LED light beams are superimposed so as to form white light.

The LEDs 1 in the embodiment are condensing type LEDs, and the diffusion angle of the projected light is approximately 10 degrees. The focal distance (described below) are obtained by appropriately adjusting the diffusion angle of the LEDs.

The disk-form substrate 3 has a central hole, thus being in a doughnut shape and is, as seen from FIG. 1, mounted in the space between the inner cylinder 21 and outer cylinder 22 which form a cylindrical housing 2. A CCD (charge coupled device) camera 4 is inserted into the interior of the inner cylinder 21 of the housing 2 from above and installed in the housing 2, so that the object of examination 7 which is illuminated by the LED illuminating device of the present invention can be imaged by this camera 4. The opitical axis of the camera 4 is aligned on the central axis Z of the housing 2.

With regard to the above-described LED assembly, a similar effect can be obtained by means of a construction that uses chip type LEDs as LED light sources with a combination of lenses or by a means of a construction that uses other LED light sources such as condensing type LED lamps, etc. Furthermore, besides using an LED assembly installed on a printed circuit board, it would also be possible to install a plurality of LED lamps in the housing 2, and to use these LED lamps as an LED assembly.

Furthermore, the housing 2 includes a doughnut-shape diffusing film 8, a doughnut-shape light collecting or light-condensing lens 6 to which a light-blocking seal 63 having a central hole is adhered, and a doughnut-shape polarizing prism 5. These elements are installed in the space between the inner cylinder 21 and the outer cylinder 22 of the housing 2.

The diffusing film 8 is obtained from a transparent material such as a plastic film, etc., which has diffusing properties.

The condensing lens 6 is installed from beneath the diffusing film 8 in FIGS. 1 and 2. The condensing lens 6 consists of a circular base 62 and a plurality of (eight in this embodiment) lens portions 61 which are disposed in a circular arrangement on the underside of the base 62 so as to form an integral element with the base 62.

The light-blocking seal 63 is an annular member and has a plurality of (eight) through-holes 64 which are formed in a circular arrangement coaxial with the respective lens portions 61 of the condensing lens 6. The light-blocking seal 63 is provided on the lens 6 so as to maintain the positional relationship with the condensing lens 6. As a different construction, it would also be possible to apply a masking treatment on the upper surface of the condensing lens 6 or to install the light-block seal 63 on the top surface of the lens 6.

The diffusing film 8 is used so as to even out the biased illumination distribution of the LEDs 1; and this could also be accomplished by applying a light-diffusing treatment such as a crinkle finish, etc. to the upper surface of the condensing lens 6.

The polarizing prism 5 is installed in the housing 2 so that a contact part 53 thereof contacts the undersurface of the inner circumferential rim of the base 62 of the condensing lens 6 from beneath and is then fastened in this position. The reference numeral 51 indicates a first polarizing surface of the prism 5, and this first polarizing surface 51 is formed on the LED side (or it faces the LEDs 1); and the reference numeral 52 indicates a second polarizing surface of the prism 5, and this second polarizing surface 52 is formed on the side that faces the surface that is to be illuminated (or it faces the opposite direction from the LEDs 1). As a result of this two-sided prism effect of the prism 5, a sufficient polarized light can be directed toward the central axis Z of the illuminating device.

The polarizing prism 5 is formed from a light-transmitting material. Any material with light-transmitting properties can provide the required effect. Accordingly, transparent synthetic resins such as methacrylic resins or AS resins, etc., as well as inorganic substances such as glass, etc. can be used as the material of the polarizing prism 5.

In use, as shown in FIG. 1 that shows the light path (only one shown) of the LED illuminating light of the present invention, the LED illuminating light collected by the resin molding of each LED 1 passes through the diffusing film 8 and is converted into illuminating light of a uniform intensity.

This light then passes through the light-blocking seal 63 and enters the condensing lens 6. Of the light entering the condensing lens 6, only the light directed onto the through-hole 64 of the light-blocking seal 63 can pass through (as a result of the effect of the light-blocking seal 63), and the remaining illuminating light is blocked so as not to be illuminated on the condensing lens 6. Thus, the light-blocking seal 63 partially blocks the LED lights, allowing only the light entering the through holes 64 to pass through the seal 63.

The light entering the condensing lens 6 is caused to be incident on the lens portions 61 and is thus further condensed, illuminating the area straightly beneath each LED 1. The area illuminated by each LED 1 in this case is limited to a spot light by the light-blocking seal 63; and further, the respective illuminated areas are made equal by making the areas of the through-hole 64 uniform.

Next, the LED illuminating light directed straightly downward enters the polarizing prism 5. As a result, the light is polarized toward the central axis Z of the LED illuminating device, first by the first polarizing surface 51 and then by the second polarizing surface 52 of the prism.

The polarization angle of the prism 5 is set so that the plurality of LED illuminating light beams are superimposed when the distance between the LED illuminating device and the illuminated surface is set at a prescribed focal distance; and therefore, the object of examination 7 is placed under the superimposed illumination of the LED illuminating light beams.

The double polarization structure of the polarizing prism 5 as described above is effective in shortening the focal distance between the LED illuminating device and an illuminated surface, so that the CCD camera 4 can be installed at a closer location to the object of examination 7. At the same time, because of such a double polarization structure, the polarization angle can be increased, so that the size of the LED illuminating device in the circumferential direction can be reduced.

If the polarization angle of the first polarizing surface 51 of the prism 5 is set to be sufficiently small, it is possible to obtain a sufficient polarization angle with the use of only one polarizing surface 51 (or without the use of the second polarizing surface 52). However, such a single surface structure (including a large light-reflecting angle) means that the angle at which the LED light enters into the prism is shallow; as a result, the efficiency of incidence of the LED light would drop, and the LED light would be blocked by the wall surface of the lower portion of the inside cylinder of the housing 2. So as to solve this problem, the wall surface of the inside cylinder of the housing 2 can be made transparent; however, with such a transparent structure, the leakage of LED light comes into the CCD camera, causing another problem.

Accordingly, as shown in FIG. 1, the LED illuminating device of the present invention employs a double polarizing structure that has a polarization angle of A° provided in the polarizing surface 51, and a polarization angle of B° provided in the polarizing surface 52, thus securing a large polarization angle and a short focal distance.

Figure 3:
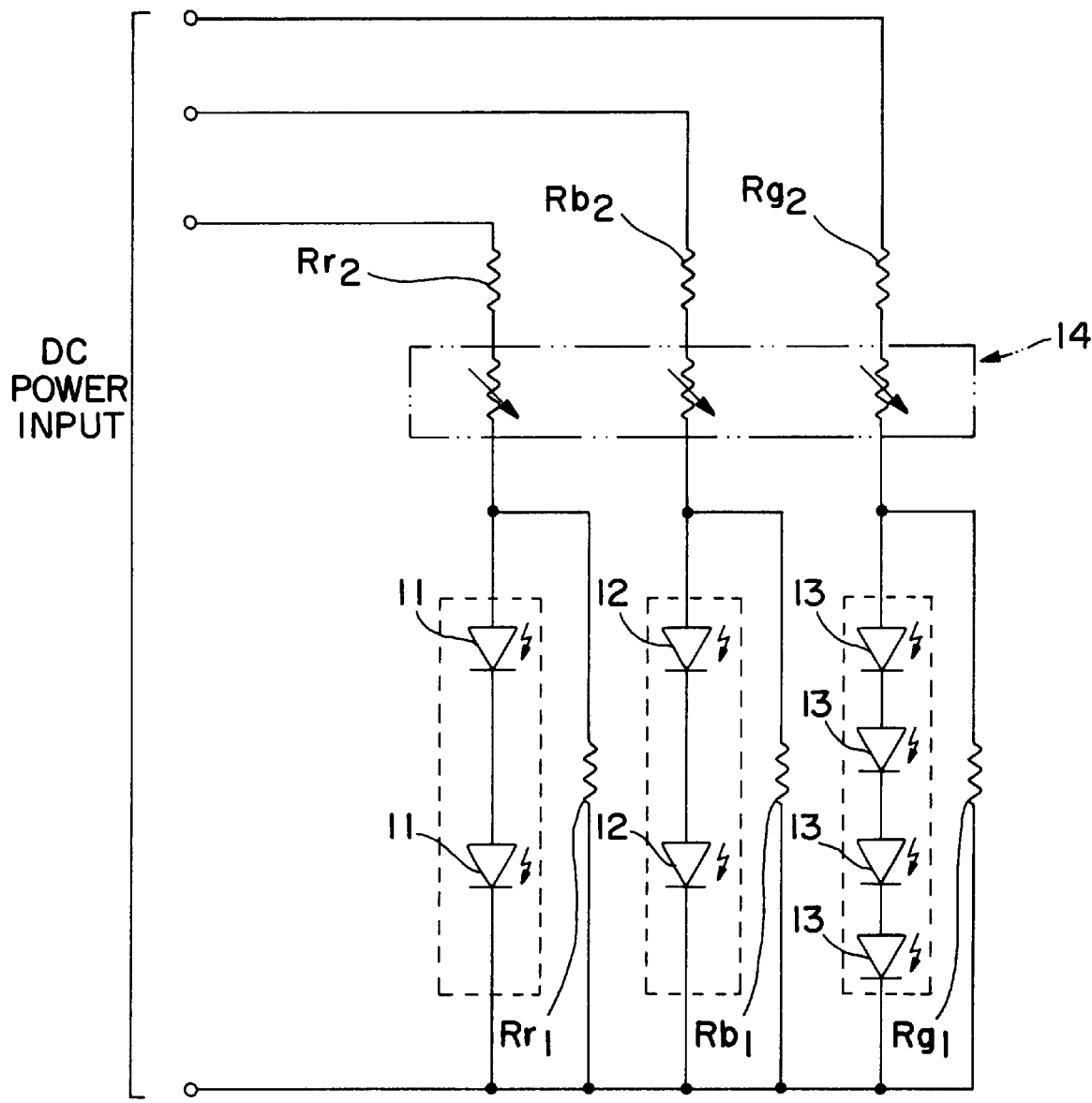
FIG. 3 is a circuit diagram of the LED illuminating device.
Figure 4:
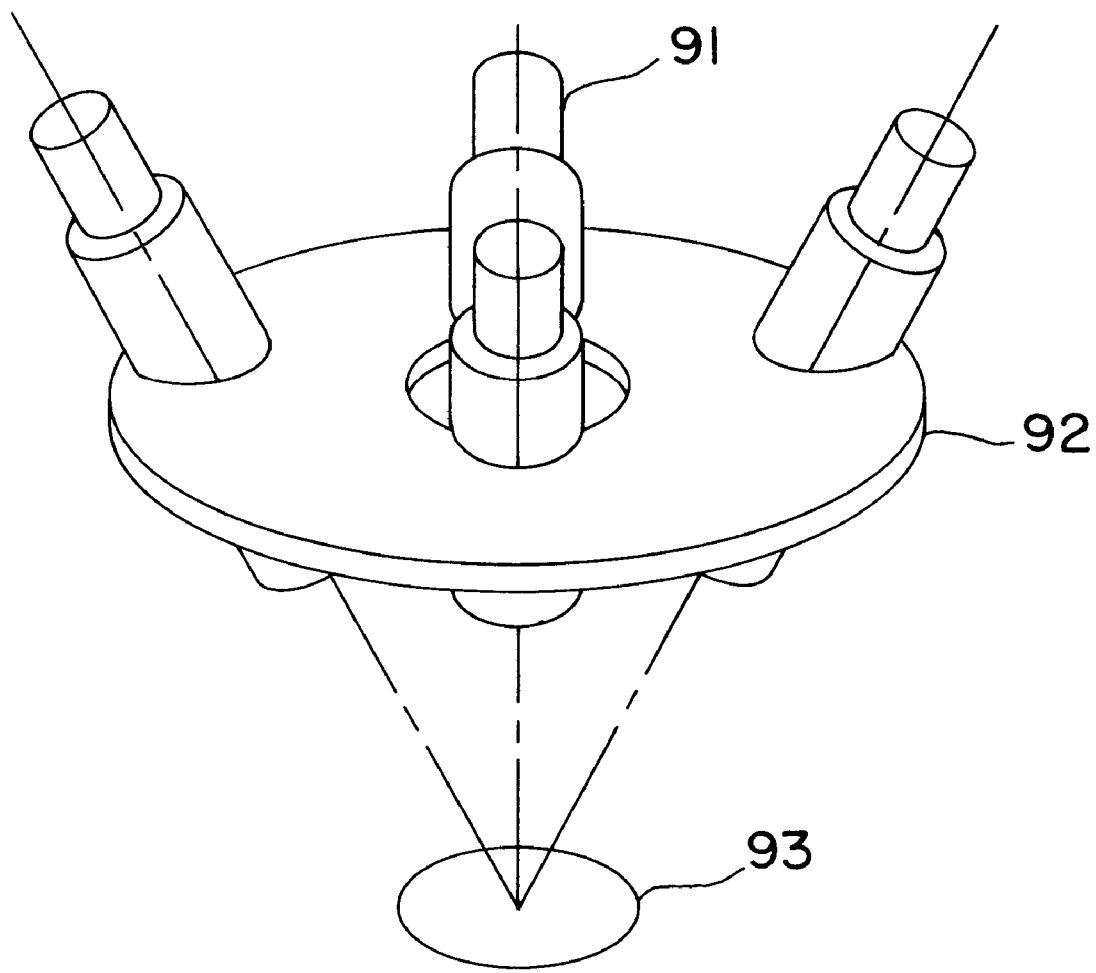
FIG. 4 is a perspective view of a conventional LED illuminating device.

FIG. 3 shows a circuit diagram of the LED illuminating device of the present invention.

The circuit includes three systems: a circuit for the red LEDs, a circuit for blue LEDs and a circuit for green LEDs. The red LED assembly includes a current-limiting resistor Rr1 which is installed in parallel with the red LEDs 11, and it further includes a light-adjusting volume 14 and current-limiting resistor Rr2 which are installed in series with the red LEDs 11. The blue LED assembly includes the current-limiting resistor Rb1 which is installed in parallel with the blue LEDs 12, and it further includes a light-adjusting volume 14 and current-limiting resistor Bb2 which are installed in series with the blue LEDs 12. The green LED assembly includes a current-limiting resistor Rg1 which is installed in parallel with the green LEDs 13, and it further includes a light-adjusting volume 14 and current-limiting resistor Rg2 which are installed in series with the green LEDs 13.

In this circuit, the brightness of illumination and the superimposition of chromaticity can be adjusted by the use of the light-adjusting volumes 14 provided for each LED group so as to adjust the current supplied to the LEDs of the respective colors.

The above-described LED illuminating device of the present invention is used together with a control unit (not shown) used for light adjustment, and they are incorporated into, for instance, an image recognition mechanism of an electronic parts mounting machine; and ordinarily, objects to be examined are positioned in close proximity to the camera 4 and illuminated. When the images obtained by the camera 4 are subjected to a preliminary analysis by the image recognition mechanism, the resulting signals are received by the control unit so that the illumination brightness and superimposition of chromaticity are adjusted for the optimal illumination conditions. In the LED illuminating device of the shown embodiment, red, blue and green LEDs are appropriately installed in the LED assembly, and the illumination brightness and chromaticity of the superimposed light beams can be adjusted by adjusting the electric current supplied to LEDs of the respective colors.

Accordingly, it is possible to provide a superimposed light with an appropriate illumination intensity and light quantity in accordance with the material and hue of the object of examination, so that a high contrast can be obtained.

In addition, according to the invention, various use configurations are possible in accordance with the objects of examination and inspection devices. For instance, the LED illuminating device may be installed under a plate on which the object of examination is placed so as to use the penetrating light.

Furthermore, it is also possible to employ LED lamps equipped with condensing lenses in which the LED resin molding is doubled, or to use a construction in which the LEDs are installed so as to face inward from a circumferential direction and the light is polarized vertically downward by means of a prism.

In addition, the polarization angle of the projected light of the LEDs is not limited to an angle of approximately 10 degrees; and it is possible to use LEDs having an angle of 30 degrees, 45 degrees, etc.

The diffusing film and light-blocking seal are not limited to the installation arrangement described above. For instance, it is possible to apply a light-diffusing treatment to the upper surface of the first reflective surface 51 of the polarizing prism 5 or to apply a light-blocking treatment to the undersurface of the condensing lens 6.

In the embodiment, the polarizing prism 5 is a single annular body with conical prism surfaces. However, it is possible to form the prism surfaces flat or to install individual prisms for each LED. The plurality of LEDs of different colors can be formed into an optimal combination for the inspection device by appropriately combining two or more types of LEDs having colors such as red, yellow, green, orange, blue, etc. In addition, various other modifications or applications to commercial products of a similar sort are possible without changing the gist of the present invention.

As seen from the above, according to the present invention, LED illuminating light is polarized and superimposed by means of a polarizing optical means. Accordingly, a bright superimposed illuminating light can be obtained by an LED assembly which is easy to manufacture by installing LEDs, for instance, upright. Thus, the present invention has a great practical merit in which an LED illuminating device of the type in which correction of the angles of the respective LEDs has been difficult in the past can easily be manufactured, and a compact and inexpensive LED illuminating device which has a simple construction is obtainable.

Furthermore, with an addition of a condensing optical means, the LED illuminating light can be converted from diffused light to spot-illumination type LED illuminating light. Thus, an increased quantity of light per unit area is obtainable.

Also, with an addition of a diffusing optical means, the irregularity in the illuminating light that is inevitable to LEDs can be evened out. Moreover, by adding a light-blocking means, illuminating light which is free of any irregularity and which has a selected illumination area can enter the condensing lens. The spot-illumination type light that is obtained on the illuminated surface after passing the condensing optical means and polarizing optical means makes superimposed light with a uniform illumination distribution which is free of any excess illumination area or irregularity in illumination.

In addition, the polarizing optical means includes two polarizing surfaces so as to increase the polarization angle and shorten the focal distance. Accordingly, the inspection device can be small in size, and it is possible to shorten the distance between the illuminating device and the object of examination. In addition, an illuminating light color which facilitates the detection of the object of examination can be obtained by arbitrarily adjusting the color of the illuminating light; accordingly, the sharpness and contrast of images obtained by the image recognition and inspection device into which the device of the present invention is incorporated can increase.

What is claimed is:

1. An LED illuminating device comprising:
   an LED assembly on which a plurality of LED elements are mounted in a prescribed arrangement;
   a polarizing optical means provided in a light beam path of said plurality of LED elements for polarizing light from said LED elements and for superimposing light from each of said plurality of LED elements at a prescribed focal distance; and
   a holding means which holds said LED assembly and said polarizing optical means;
   whereby illuminating light of a uniform intensity is provided.

2. An LED illuminating device characterized in that said device comprises:
   an LED assembly on which a plurality of LED elements are mounted in a prescribed arrangement;
   a condensing optical means and a polarizing optical means provided successively in a light beam path of said plurality of LED elements; and
   a holding means which holds said LED assembly, condensing optical means and polarizing optical means, and wherein
   LED illuminating light beams are susperimposed at a prescribed focal distance.

3. An LED illuminating device characterized in that said device comprises:
   an LED assembly on which a plurality of LED elements are mounted in a prescribed arrangement;
   a condensing optical means, a diffusing optical means, a polarizing optical means and a partially light-blocking means provided successively in a light beam path of said plurality of LED elements; and
   a holding means which holds said LED assembly, condensing optical means, diffusing optical means, polarizing optical means and light-blocking means; and wherein
   LED illuminating light beams are superimposed at a prescribed focal distance.

4. An LED illuminating device according to claim 2 or 3, wherein said polarizing optical means is a polarizing prism which includes a first polarizing surface formed on a source thereof that faces said LEDs and a second polarizing surface formed on a surface thereof facing a surface that is to be illuminated.

5. An LED illuminating device according to claim 2 or 3, wherein said plurality of LED elements comprises LED elements of a plurality of colors, and a control means is provided for controlling a quantity of light of said LED elements.

6. An LED illuminating device according to claim 4, wherein said plurality of LED elements comprises LED elements of a plurality of colors, and a control means is provided for controlling a quantity of light of said LED elements.

7. An illuminating device characterized in that said device comprises:
   a device housing comprising a hollow cylindrical body;
   a plurality of LEDs provided in said device housing so as to be arranged circularly near one end of said device housing; and
   a doughnut-shape polarizing optical means provided near another end of said device housing, said polarizing optical means having at least one diffusion surface so as to polarize from said LEDs and for superimposing light from each of said plurality of LEDs at a prescribed focal distance;
   whereby illuminating light of a uniform intensity is provided.

8. An illuminating device characterized in that said device comprises:
   a device housing comprising a hollow cylindrical body;
   a plurality of LEDs provided in said device housing so as to be arranged circularly near one end of said device housing;
   a doughnut-shaped polarizing optical means provided near another end of said device housing, said polarizing optical means having at least one diffusion surface so as to polarize light from said LEDs; and
   a doughnut-shaped condensing optical means provided between said plurality of LEDs and said polarizing optical means, said condensing optical means comprising a plurality of lens surfaces which are arranged so as to positionally correspond to said plurality of LEDs.

9. An illuminating device according to claim 8, wherein said plurality of LEDs emit different colors.

10. An illuminating device according to claim 8 or 9, further comprising a imaging means provided at said one end of said device housing, an optical axis of said imaging means being aligned on a center axis of said cylindrical device housing so that said lights from said LEDs are polarized toward said optical axis of said imaging means.

* * * * *